United States Patent [19]
Taylor

[11] 3,979,828
[45] Sept. 14, 1976

[54] DENTAL PROSTHETIC DEVICE AND PROSTHETIC DENTISTRY METHOD

[76] Inventor: Bill E. Taylor, 617 S. Quincy, Enid, Okla. 73701

[22] Filed: Sept. 20, 1974

[21] Appl. No.: 507,946

[52] U.S. Cl. ................................................. 32/10 A
[51] Int. Cl.² .......................................... A61C 13/00
[58] Field of Search .................................. 32/10 A

[56] References Cited
UNITED STATES PATENTS

| 581,335 | 4/1897 | Carr | 32/10 A |
|---|---|---|---|
| 3,576,074 | 4/1971 | Gault | 32/10 A |
| 3,589,011 | 6/1971 | Sneer | 32/10 A |

FOREIGN PATENTS OR APPLICATIONS

| 1,228,362 | 3/1960 | France | 32/10 A |

*Primary Examiner*—Robert Peshock
*Attorney, Agent, or Firm*—Dunlap, Codding & McCarthy

[57] ABSTRACT

An improved prosthetic dentistry method and an improved dental prosthetic device wherein the prosthetic device includes an implant disposable in a fresh extraction site or a surgically produced extraction site as the patient conditions dictate, and a crown removably attachable to the implant. The implant has a configuration shaped to encourage hard tissue and bone ingrowth into and through portions of the implant for increasing the mechanical interlock between the implant and the existing alveolar bone. In practice, the implant is inserted into the socket opening formed at the extraction site and, after a healing period sufficient to assure the required mechanical interlock, the crown is secured to the implant, thereby providing a free-standing dental prosthetic device which does not require the adjacent teeth for support purposes. The crown would preferably be attached immediately in those instances involving the replacement of anterior teeth.

10 Claims, 7 Drawing Figures

DENTAL PROSTHETIC DEVICE AND PROSTHETIC DENTISTRY METHOD

DESCRIPTION OF THE PREFERRED EMBODIMENTS

Figure 1:
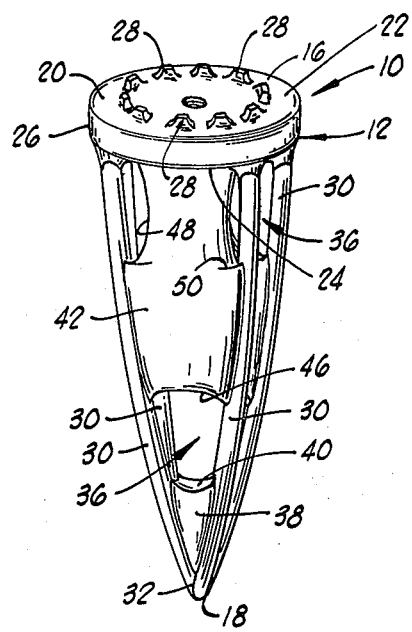
FIG. 1 is a partial perspective of the implant of the dental prosthetic device of the present invention.
Figure 2:
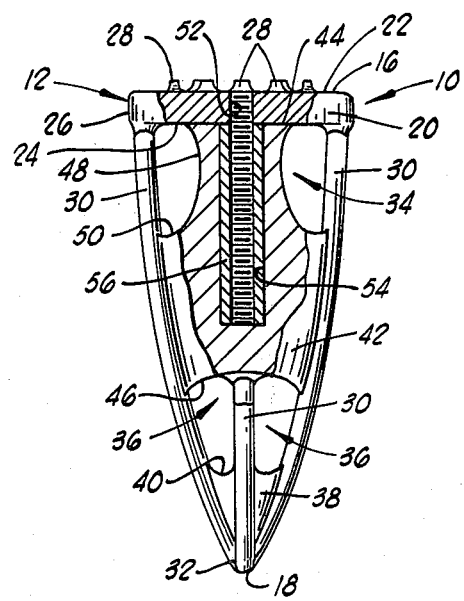
FIG. 2 is a sectional view of the implant of FIG. 1.

In general, the present invention includes an improved prosthetic dentistry method for replacing lost natural teeth and an improved dental prosthetic device. The method and the prosthetic device of the present invention can be utilized to replace natural teeth immediately following the loss of the natural tooth or teeth, and also can be utilized to replace natural teeth at a time along after the loss.

Referring more particularly to the prosthetic device of the present invention, one preferred embodiment of the prosthetic device is shown in FIGS. 1, 2, 3 and 4, and designated therein via the general reference numeral 10, various component portions of the prosthetic device 10 being shown in each of the four figures (FIGS. 1–4). In general, the prosthetic device 10 includes an implant 12 and a crown 14, the crown 14 being shown in FIG. 4 attached to the implant 12.

The implant 12 has an overall, generally conically shaped, geometric configuration, having an upper end 16 and a lower end 18. The implant 12 includes a circularly shaped plate 20 having an upper end face 22 forming the upper end 16 of the implant 12, a lower face 24 and an outer peripheral surface 26 extending annularly about the plate 20.

A plurality of protrusions 28 are secured to the upper face 22, each of the protrusions 28 extending a distance upwardly or perpendicularly from the upper face 22 (only some of the protrusions 28 being designated in the drawings via a reference numeral for clarity). The protrusions 28 are disposed between the outer surface 26 and the central portion of the plate 20, and the protrusions 28 are disposed annularly about the upper face 22, protrusion 28 being spaced from the adjacent protrusions 28. The protrusions 28 cooperate in securing a crown 14 to the plate 20 in a manner to be described in greater detail below.

A plurality of rods 30 are connected to the lower face 24 of the plate 20, and each rod 30 has a circularly shaped cross-section, in one preferred form, each of the rods 30 extending from the plate 20 generally between the upper end 16 and the lower end 18 of the implant 12. More particularly, one end of each rod 30 is secured to the lower face 24 generally near the outer surface 26, and the opposite end of each rod 30 is secured at a common connection 32 forming the lower end 18 of the implant 12. The rods 30 are spaced circumferentially about the plate 20 and the portion of each rod 30, generally between the connection to the plate 20 and the common connection 32, is formed on a slight curve tapering inwardly toward the common connection 32.

The rods 30 extend about and define the outer circumferential limits of an open space 34 formed between the lower face 24 of the plate 20 and the common connection 32 of the lower end 18 of the implant 10. The rods 30 are spaced a distance apart forming an opening 36 between each rod 30 and the adjacent rods 30. The openings 36 and the space 34 provide communication through the implant 12 and about the rods 30 for reasons to be described in greater detail below.

In one preferred form, the ends of each rod 30, opposite the ends connected to the plate 20, are securedly connected via welding or the like and the weld material cooperates to form the common connection 32, the weld material being designated in FIGS. 1–4 via the general reference numeral 38 and sometimes referred to herein as the filler 38. The filler 38 extends a distance from the common connection 32 toward the plate 20 terminating with an upwardly facing surface 40 disposed within the open space 34 and positioned between the upper and the lower ends 16 and 18 of the implant 12, portions of the filler 38 being securedly affixed to the adjacent portions of each rod 30. The filler 38 securedly affixes the end of the rods 30 and enhances the structural integrity and mechanical interlock of the implant 12.

A base 42, having an upper end 44 and a lower end 46, is disposed within the space 34. The upper end 44 of the base 42 is secured to a central portion of the lower face 24 of the plate 20 and the base 42 extends a distance from the plate 20 toward the lower end 18 of the implant 12 terminating with the lower end 46 of the base 42. Portions of the base 42, extending generally from the lower end 46 toward the upper end 44 of the base 42, are connected or secured to each of the rods 30. The portions of the base 42 connected to each of the rods 30 enhance the structural integrity of the implant 12 via providing a solid interconnection between the rods 30 spaced between the solid interconnections provided via the plate 20 and the common connection 32 in cooperation with solid interconnection provided via the filler 38.

A recess 48 is formed in the base 42. The recess 48 extends annularly about the base 42 intersecting the upper end 44 and extends a distance from the upper end 44 of the base 42 toward the lower end 46 thereof terminating with an upwardly facing surface 50. The upwardly facing surface 50 is positioned within the space 34 generally between the lower surface 24 of the plate 20 and the lower end 18 of the implant 12. More particularly, the upwardly facing surface 50 is positioned between the lower surface 24 of the plate 20 and the upwardly facing 40 of the filler 38, the upwardly facing surfaces 40 and 50 providing a pair of surfaces disposed within the space 34 and spaced between the upper and the lower ends 16 and 18 of the implant 12. The lower end 46 of the base 42 is spaced a distance from the filler 38 upwardly facing surface 40 to maintain the portion of the space 34 therebetween open.

The base 42 fills a portion of the space 34 and the recess 48 reduces the portion of the space 34 filled via the base 42. Further, the recess 48 is formed adjacent and intersecting the upper end 44 of the base 42, thereby maintaining a substantial portion of the space 34 adjacent and near the lower face 24 of the plate 20 open or, in other words, maintaining a substantial portion of the lower face 24 exposed. The base 42 is constructed and shaped to enhance and augment the structural integrity and the mechanical interlock of the implant 12, including the structural integrity between the spaced rods 30, and to provide a solid element structure connected to the lower face 24 of the plate 20 and extending a distance therefrom while maintaining a substantial portion of the space 34 open, particularly adjacent and near the lower face 24 of the plate 20.

A threaded opening 52 is formed through a central portion of the plate 20 intersecting the upper face 22 and the lower face 24 thereof. Another opening 54 is formed in the base 42 intersecting the upper end 44 and extending a distance through the base 42 toward the lower end 46. The diameter of the opening 54 is larger than the diameter of the threaded opening 52 and an insert 56 is disposed in the base 42 opening 54. The insert 56 has a threaded opening 58 extending therethrough. In an assembled position, the base 42 is secured to the plate 20 and positioned such that the plate 20 threaded opening 52 is aligned with the base 42 threaded opening 58 formed through the insert 56.

It should be noted that, in one preferred form, the base 42 and the plate 20 are constructed from a single piece of material to provide a unitary construction.

The prosthetic device 10 includes a fastener 60 having an elongated, threaded member 62 and a head 64, the threaded member 62 extending a distance from the head 64. The head 64 is generally cylindrically shaped and is connected to one end of the threaded member 62, the head 64 extending a predetermined distance 66 from the end of the threaded member 62 connected thereto, the distance 66 being sometimes referred to herein as the height 66 of the head 64. A recess 68 is formed in the end of the head 64, opposite the end connected to the threaded member 62, the recess 68 being shaped for receiving a tool (not shown) for turning threaded fasteners and the like such as a screw driver like tool, for example. The threaded member 62 is threadedly insertable and threadedly removable through the aligned threaded openings 52 and 58 in the plate 20 and the base 42, respectively.

Figure 3:
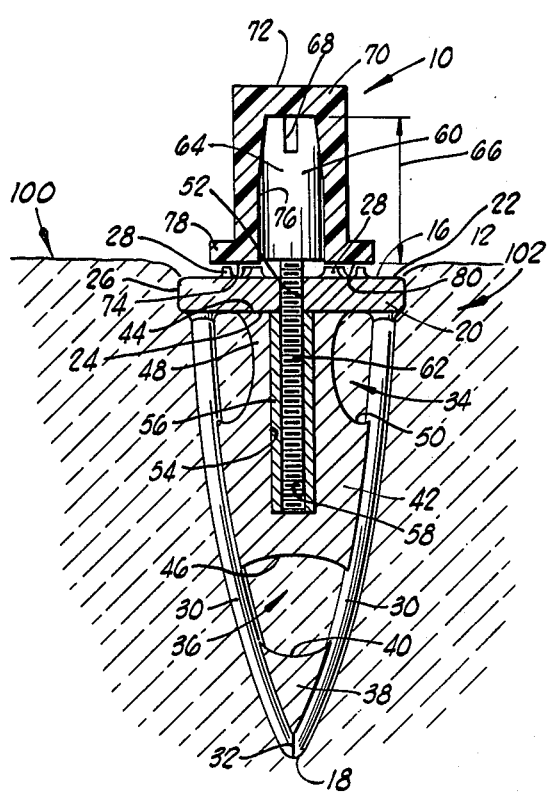
FIG. 3 is a sectional view of the implant of FIGS. 1 and 2 with a temporary cap (sometimes referred to in the art as a "transfer coping") removably affixed thereto, the implant being disposed in a socket opening formed at an extraction site.

In one aspect of the present invention, as shown in FIG. 3, the prosthetic device 10 includes a cap 70 having an upper end 72 and a lower end 74. The cap 70 is generally cylindrically shaped and has an opening 76 intersecting the lower end 74 and extending a distance through the cap 70 toward the upper end 72 thereof. A flange 78 is formed on the outer peripheral surface of the cap 70 generally adjacent the lower end 74, the flange 78 extending a distance radially from and circumferentially about the cap 70. The lower end 74 and one surface of the flange 78 form a downwardly facing surface 80 extending annularly about the opening 76.

In one preferred form, the cap 70 is constructed of a material compatible with the oral disposition of the cap 70 during one aspect of the implant utilization as contemplated via the present invention. In one preferred form, the opening 76 has a diameter slightly smaller than the diameter of the fastener 60 head 64 and the opening 76 extends through the cap 70 for a distance at least equal to the height 66 of the fastener 60 head 64. During one aspect of the operation of the present invention, the cap 70 is disposed over the fastener 60 head 64, the fastener 60 head 64 being inserted into the cap 70 opening 76 to a position wherein the downwardly facing surface 80 engages the uppermost ends of the protrusions 28 limiting the movement of the cap 70 over the fastener 60 head 64. The cap 70 is shaped to allow the fastener 60 head 64 to be inserted within the cap 70 opening 76, yet the shape of the cap 70 is such that the cap 70 is securedly disposed over the fastener 60 head 64, the diameter of the cap 70 opening 76 being slightly larger than the diameter of the fastener 60 head 64.

Figure 4:
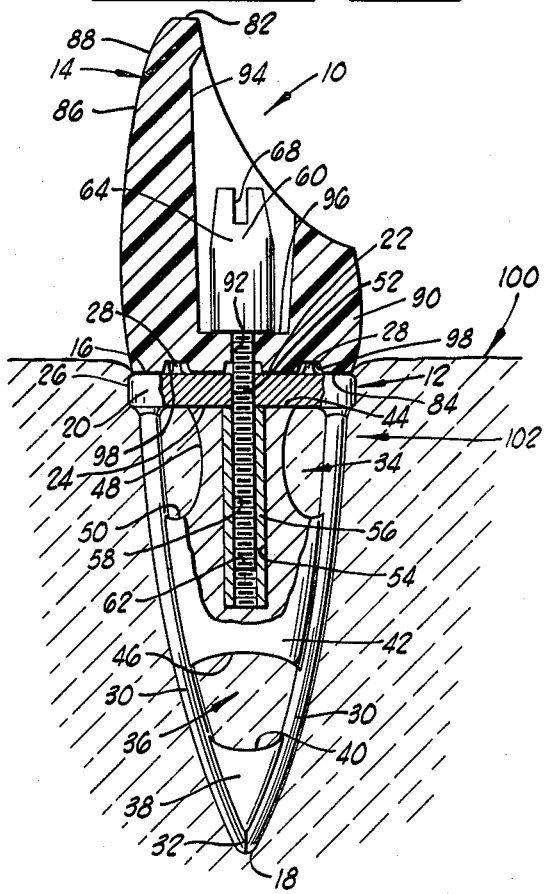
FIG. 4 is a sectional view of the implant, similar to FIG. 3, but showing the crown securedly affixed thereto.

In one other aspect of the present invention, the crown 14 of the prosthetic device 10 is secured to the implant 12, the crown 14 having an upper end 82, a lower end 84, and an outer peripheral surface 86, as shown in FIG. 4. It should be noted that the "crown" is utilized herein to generally designate dental prosthetic component simulating the visible portion of a tooth extending substantially above the gingival tissue and resembling a natural tooth.

The outer peripheral surface 86 of the crown 14 includes an anterior portion 88 and a posterior portion 90, the side portions (not shown in the drawings) of the outer peripheral surface 86 being generally disposed near adjacent teeth with the exception of the rearwardmost molar teeth (the third molar, for example). The crown 14 is shown in FIG. 4 as having a general shape in the form of an incisor for the purpose of illustrating the operation and nature of the present invention, and it is specifically understood that neither the method nor the apparatus is limited to the replacement of any particular tooth; rather, the method and apparatus of the present invention are useful for replacing any tooth regardless of the particular oral disposition of the tooth to be replaced.

An opening 92 is formed through a central portion of the crown 14 intersecting the upper end 82 and the lower end 84, and a recess 94 is formed through the upper end 82 of the crown 14, the recess 94 having a diameter larger than the diameter of the opening 92 and extending a distance toward the lower end 84 terminating with an upwardly facing surface 96 disposed with a portion of the crown 14. The opening 92 intersects the recess 94, and the recess 94 extends through the crown 14 to a depth sufficient to receive and to accommodate the head 64 of the fastener 60. A plurality of circumferentially spaced depressions 98 are formed in the lower end 84 of the crown 14 (only two of the depressions 98 being shown in FIG. 4 for clarity), and each of the depressions 98 is sized to receive a portion of one of the protrusions 28 formed on the plate 20, each of the protrusions 28 being disposed in one of the depressions 98 and engaging the adjacent portions of the crown 14 formed via the depressions 98 to prevent rotational movement of the crown 14 in an assembled position of the crown 14 on the plate 20.

OPERATION OF FIGS. 1 THROUGH 4

The prosthetic device 10 described in detail before is utilized in the prosthetic dentistry method of the present invention to provide an artificial replacement for the root and crown portions of a tooth. In general, a tooth may be prematurely lost via some accidental occurrence or the like, or as a result of the tooth having to be removed by force or extracted for some dental health reason. In either event, when the prosthetic dentistry method of the present invention is applied within a relatively short period of time after the extraction or removal of a tooth, the remaining extraction site may be sufficient to accommodate the immediate insertion of the implant 12 with little or no additional surgery, the extraction site in those instances being referred to sometimes herein as the "fresh extraction site" for clarity. In other instances, a tooth may have been missing for a period of time such that the former extraction site has been partially or completely closed via normal healing processes. In these latter instances, the closed or partially closed extraction site must be opened surgically to provide the required extraction site for receiving and accommodating the implant 12. The surgical methods for preparing and opening an extraction site for receiving and accommodating an implant simulating the root portion of a tooth are well-known in the art of dentistry and need not be described in detail herein.

The term "extraction site" is used herein to generally refer to the opening in the gingival tissue and the alveolar bone remaining after the root portion of a tooth has been removed and extracted and to the opening formed in the gingival tissue and the alveolar bone for accommodating a dental prosthetic device, particularly the root simulation portion of such prosthetic device. In one sense, the term extraction site is used herein to generally refer to an oral location where an opening is to be formed in the gingival tissue and the alveolar bone for receiving and accommodating the root simulation portion of a dental prosthetic device.

After the extraction site has been prepared for receiving and accommodating the root simulation portion of the prosthetic device 10 or, more particularly, the implant 12, the implant 12 is inserted into the opening formed at the extraction site, the lower end 18 of the implant 12 being first inserted into the extraction site opening and the implant 12 being disposed in the extraction site opening to a position wherein the upper end 16 is positioned generally near the outer surface formed via the gingival tissue. The height of the implant 12 between the upper end 16 and the lower end 18 thereof approximates the height of the natural tooth root portion being replaced and, more particularly, the height of the implant 12 is sufficient such that a substantial portion of the implant 12 is disposed below the gingival tissue outer surface. The gingival tissue outer surface is diagrammatically illustrated in FIGS. 3 and 4, and designated therein via the general numerical reference 100, the gingival tissue below the outer surface 100 and the portion of the alveolar bone thereunder being shown in FIGS. 3 and 4 designated therein via the general reference numeral 102 for clarity.

After the implant 12 has been disposed and properly positioned in the socket opening formed at the extraction site, as diagrammatically illustrated in FIGS. 3 and 4, the gingival tissues are trimmed to accommodate the gingiva to the shape of the root portion of the implant 12, the gingival tissues being positioned around the inserted portion of the implant 12 in a manner approximating the position of the gingival tissues about the root portion of the tooth being replaced via the prosthetic device 10. After the root portion of the implant 10 has been positioned in the socket opening formed at the extraction site and the gingival tissues have been properly positioned around the inserted implant 12, the fastener 60 is threadedly inserted through the threaded opening 52 formed through the plate 20 and through the threaded opening 58 formed through the insert 56 to a position wherein the fastener 60 head 64 is disposed near the upper face 22 of the plate 20, as shown in FIG. 3. The resilient cap 70 is then disposed over the fastener 60 head 64 to a position wherein the cap 70 substantially encompasses the fastener 60 head 64 and the lower end 74 of the cap 70 is positioned near or adjacent the uppermost ends of the protrusions 28. It should be noted that the fastener 60 can be threadedly secured within the threaded openings 52 and 58 and the cap 70 can be disposed over the head 64 of the fastener 60 prior to inserting the implant 10 into the socket opening formed at the extraction site, this being a preferred sequence of steps since the possibilities of disturbing the position of the implant 12 in the socket opening are substantially reduced.

A temporary crown (not shown) is then secured over the cap 70 and portions of the temporary crown are then secured to adjacent teeth to maintain the implant 12 securely positioned within the socket opening formed at the extraction site during the healing period. The construction of a temporary crown for securely positioning the implant 12 in a manner briefly described before is well-known in the art of dentistry and it is not deemed necessary to illustrate or describe any particular temporary crown construction or composition.

Thus, the implant 12 is positioned in the socket opening formed at the extraction site such that blood flows freely through the space 36 between the rods 30 and through the open space 34 existing between the upwardly facing surface 40 of the filler 38 and the surface formed via the lower end 46 of the base 42 during a portion of the healing period. The implant 12 is also positioned in the socket opening at the extraction site such that blood flows freely through the space 36 between the rods 30 and through the open space 34 existing between the upwardly facing surface 50 formed on the base 42 and the lower face 24 of the plate 20, blood also flowing about the outer peripheral surface of the neck portion formed on the base 42 via the annular recess 48 during a portion of the healing period.

During the healing period while the implant 12 is maintained in a predetermined position within the socket opening at the extraction site via the interconnection between the temporary crown and the adjacent tooth or teeth, as the case may be, hard and soft tissue grow into and through the portions of the open space 34 of the implant 12 resulting in a hard tissue and bone ingrowth into the implant 12 or, more particularly, into and through the portions of the open space 34 within the implant 12. The hard tissue and bone ingrowth into the implant 12 results in a mechanical interlock between the alveolar bone and the implant 12 thereby securing the implant 12 in a free-standing position within the socket opening at the extraction site. Further, some fibrous membranous tissue may form between portions of the newly formed and existing alveolar bone and the adjacent portions of the implant 12 further enhancing the mechanical interlock between the alveolar bone and the implant 12.

The hard tissue and bone ingrowth within the open space 34 between the downwardly facing surface formed via the lower end 46 of the base 42 and the upwardly facing surface 40 of the filler 38 and about the adjacent portions of the rods 30 provides one aspect of the mechanical interlock between the newly formed hard tissue and bone ingrowth into the implant 12 configuration at one level between the upper end 16 and the lower end 18 of the implant 12. The hard tissue and bone ingrowth within the portion of the open space 34 formed between the upwardly facing surface 50 of the base 42 and the lower face 24 of the plate 20 and the adjacent portions of the rod 30 provides another aspect of the mechanical interlock between the hard tissue and bone ingrowth and the implant 12, the latter-mentioned aspect of the mechanical interlock being spaced from the first-mentioned aspect of the mechanical interlock via an interposed portion of the base 42. Thus, the geometric configuration of the implant 12 is shaped to increase the surface area of the implant 12 available for forming and enhancing the mechanical interlock between the implant 12 and the hard tissue and bone ingrowth, while maintaining the size of the implant 12 within practical limits for insertion into a socket opening at an extraction site, the upwardly facing surface 40 formed on the filler 38 and the upwardly facing surface 50 formed on the base 42, each providing spaced surfaces with the space 34 for engaging a substantial quantity of hard tissue and bone ingrowth and resisting the removal of implant 12 from the socket opening.

In addition to the hard tissue and bone ingrowth into the implant 12, some membranous tissue may form between the newly formed alveolar bone matter and the adjacent, exposed portions of the implant 12, the newly formed membranous tissue connecting the newly formed alveolar bone with the exposed portions of the implant 12 and augmenting the mechanical interlock between the implant 12 and the alveolar bone, thereby enhancing the free-standing, permanent positioning of the implant 12. It should be noted that the spaced upwardly facing surfaces 40 and 50 are provided in the implant 10 and the overall configuration of the implant 10 is constructed to substantially assure a relatively secure mechanical interlock independent of the degree to which any fibrous, membranous tissue may form between the alveolar bone and the implant 12.

After the implant 12 has been sufficiently secured in position within the socket opening at the extraction site via the hard tissue and bone ingrowth into the implant 12 configuration, the temporary crown is removed and an impression is made for the purpose of preparing a custom or permanent crown, the impression being made in the usual manner well-known in the art of dentistry. It should be noted that the cap 70 is left positioned over the fastener 60 head 64 while the impression is being made, and the cap 70 will be embedded in the impression when the impression is removed. After the removal of the impression with the cap 70 embedded therein, another cap 70 is placed over the fastener 60 head 64, it being understood that all such caps 70 are substantially identical in construction to facilitate such interchangeability. After the impression has been made, the temporary crown is again disposed over the replaced cap 70 and secured to the adjacent tooth or teeth, as the case may be, while the custom or permanent crown is being made. It is particularly important that the impression is utilized solely for the purpose of identifying the spacial relationship between the existing teeth relative to the space for accommodating the custom or permanent crown, since the fit between the permanent crown, such as the crown 14 shown in FIG. 4, for example, and the implant 12 is predetermined via the predetermined sizing of the implant 12 and the crown 14, including the predetermined, known interconnection between the implant 12 and the crown 14.

After the custom or permanent crown has been prepared, the temporary crown is again removed. The cap 70 is removed from the fastener 60 head 64 and the fastener 60 is removed from the threaded openings 52 and 58 thereby exposing the upper face 22 of the implant 12. As shown in FIGS. 3 and 4, the implant 12 is positioned in the socket opening at the extraction site such that the upper face 22 of the plate 20 is disposed above the outermost surface of the gingival tissue to facilitate the interconnection of the implant 12 and the crown 14 after the implant 12 has been secured in the socket opening. In practice, the upper face 22 of the plate 20 may be disposed below the outermost surface of the gingival tissue in some instances, the primary consideration being that the upper face 22 remains substantially exposed so the crown may be connected thereto.

The permanent crown is then positioned on the upper face 22 of the plate 20 and secured in position via the fastener 60.

Referring to the permanent crown 14 shown in FIG. 4, the crown 14 is disposed on the upper face 22 of the plate 20 and positioned such that each of the protrusions 28 are disposed in one of the depressions 98 formed in the lower end 84 of the crown 14. Immediately prior to disposing the protrusions 28 in the depressions 98, the crown 14 is rotated to properly orient the anterior portion 88 and the posterior portion 90 of the crown 14 in a predetermined oral disposition. After the crown 14 has been properly positioned on the implant 12, the threaded member 62 of the fastener 60 is disposed through the opening 92 in the crown 14 and the crown 14 is secured to the implant 12 via the fastener 60 engaging portions of the crown 14 and portions of the implant 12, as shown in FIG. 4.

As mentioned before, the diameter of the head 64 is larger than the diameter of the opening 92 in the crown 14. As the fastener 60 is threaded through the opening 58, the head 64 engages a portion of the surface formed in the crown 14 via the recess 94 and cooperatingly moves the crown 14 into an assembled position on the implant 12 wherein the lower end 84 of the crown 14 abuts the upper face 22 of the plate 20, the head 64 engaging the crown 14 and securing the crown 14 in an assembled position on the implant 12. It will be apparent from the foregoing that the opening 92 does not need to be threaded and, in fact, the opening 52 in the plate 20 does not need to be threaded since the crown 14 is secured to the implant 12 via the engagement between the threaded member 62 and the threaded opening 58.

After the crown 14 had been secured to the implant 12 via the fastener 60, the space formed in the crown 14 via the recess 94 is filled with a suitable filler material (not shown) and shaped to conform to the overall configuration of the crown 14.

In the event it becomes necessary to remove the crown 14 for replacement or repair at any time in the furture, the filler material previously disposed in the recess 94 is simply removed to the extent of exposing the recess 68 in the uppermost end of the fastener 60 head 64 and the fastener 60 is unthreaded, thereby disconnecting the crown 14 from the implant 12. After the crown 14 has been repaired or after a replacement crown has been made, the repaired or replacement crown 14 is positioned on the implant 12 and secured thereto in a manner exactly like that described before. Thus, the implant 12 remains a free-standing permanent portion of the prosthetic device 10 facilitating the easy replacement or repair of the crown portion and the prosthetic device 10 remains independent of the remaining teeth or other prosthetic devices for the purpose of supporting structures.

It is significant to note that the threaded openings 52 and 58 are sealed via the base 42 so that blood will not flow through the openings 52 and 58 after the implant 112 has been inserted in the socket opening formed at the extraction site. This structure substantially eliminates the possibility of corrosion of the threaded portions of the openings 52 and 58, and substantially reduces odor problems which might otherwise occur.

EMBODIMENT OF FIGS. 5 AND 6

Figure 5:
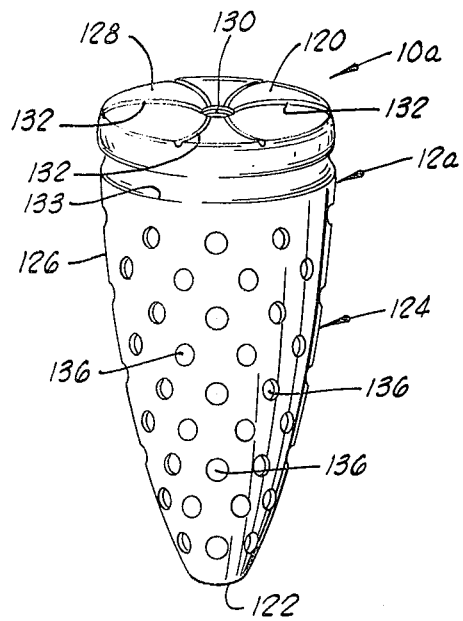
FIG. 5 is a view similar to FIG. 1, but showing a modified implant.
Figure 6:
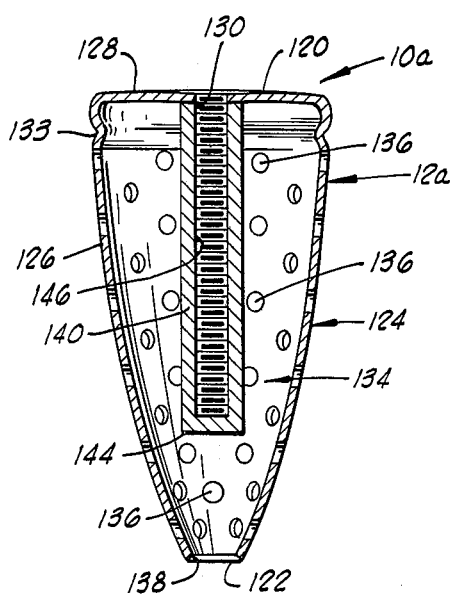
FIG. 6 is a section view of the modified implant of FIG. 5.
Figure 7:
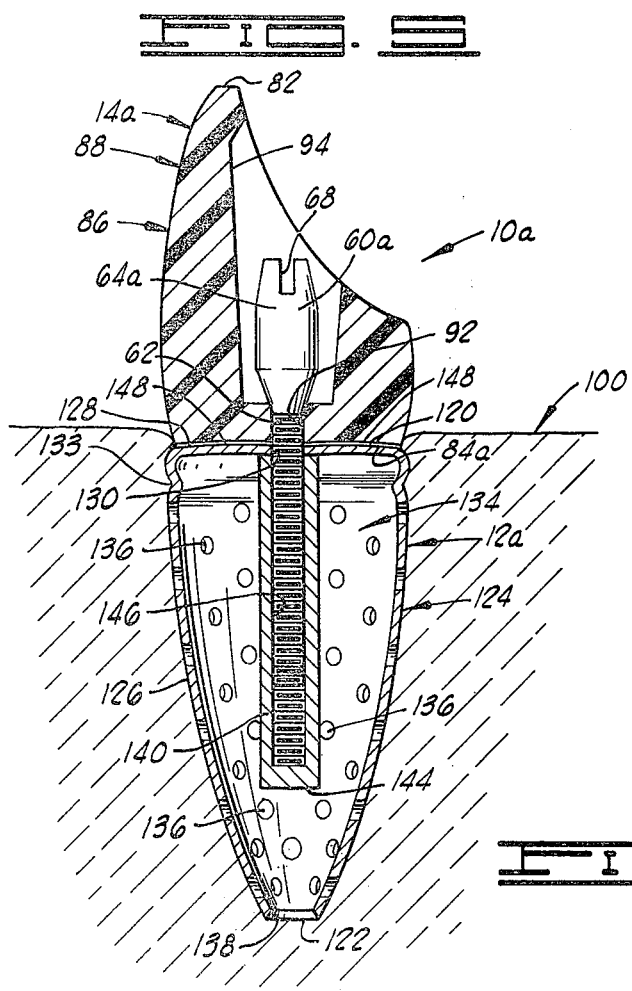
FIG. 7 is a sectional view of the modified implant of FIGS. 5 and 6, but showing a modified crown securedly affixed thereto.

Shown in FIGS. 5, 6 and 7 is a modified implant 12a having an upper end 120 and a lower end 122. The implant 12a has a body 124 having an overall generally conical shape with a wall 126 extending between the upper end 120 and the lower end 122 and tapering inwardly toward the lower end 122, the wall 126 extending circumferentially about the implant 12a body 124. The body 124 has an upper face 128 which is slightly tapered in a downwardly direction toward the central portion thereof and an opening 130 is formed through the central portion of the upper face 128.

A plurality of circumferentially spaced, radially extending grooves 132 are formed in the upper face 128. Each of the grooves 132 extends from the outer peripheral surface of the upper face 128 toward the central portion thereof, one end of each groove 132 intersecting the opening 130. An annular recess 133 is formed in the wall 126 of the body 124, the recess 133 being spaced a distance from the upper end 120 and extending circumferentially about the implant 12a body 124.

The body 124 surrounds and encompasses a space 134 and a plurality of openings 136 are formed through the body 124 wall 126 (only some of the openings 136 are designated via a reference numeral in the drawings for clarity). Each of the openings 136 intersects the space 130 and provides a communication with space 130 through the body 124 wall 126. An opening 138 is formed through the lower end 122 of the body 124 wall 126, the opening 138 intersecting and communicating with the space 130.

A rod 140, having an upper end 142 and a lower end 144, is connected to the body 124 and disposed within a portion of the space 134. A threaded opening 146 is formed through a portion of the rod 140, the opening 146 intersecting the upper end 142 and extending a distance toward the lower end 144 of the rod 140. More particularly, the upper end 142 of the rod 140 is connected to the body 124 and positioned such that the threaded opening 146 is aligned with the opening 130 formed through the body 124 upper face 128. The lower end 144 of the rod 140 is closed and the opening 146 is sealed from the space 134 via the closed, lower end 144 and the connection of the rod 140 upper end 142 and the body 124, thereby preventing the flow of blood into the threaded opening 146 during the healing period of time for reasons described before with respect to the prosthetic device 10.

The prosthetic device 10a also includes a modified crown 14a which is constructed exactly like the crown 14 shown in FIG. 4, except the lower end 84a is shaped on a slight curve to matingly engage the upper face 128 of the body 124 and a plurality of ridges 148 are formed on the crown 14a lower end 84a. Each of the ridges 148 extends from a point near the outer peripheral surface 86 radially inwardly toward the central portion of the lower end 84a, the ridges 148 being circumferentially spaced about the lower end 84a. The ridges 148 are sized and spaced such that each of the ridges 148 is matingly disposed in one of the grooves 132 to secure the crown 14a in an assembled position on the upper face 128 of the implant 12a in a manner substantially preventing rotational movement of the crown 14a.

The modified implant 10a includes a modified fastener 60a which is constructed exactly like the fastener 60 described before except the outer diameter of the fastener 60a head 64a generally adjacent the lower end thereof (opposite the end having the recess 68 formed therein) is slightly smaller than the diameter of the opening 92 in the crown 14a, and the outer peripheral surface is tapered slightly outwardly toward the end of the head 64a. Thus, a portion of the head 64a generally adjacent the end thereof, opposite the recess 68 end, is disposed with the opening 92 and the head 64a is shaped to more firmly engage the crown 14a as the fastener 60a is threaded into a position securing the crown 14a to implant 12a.

OPERATION OF FIGS. 5, 6, AND 7

The prosthetic device 10a will operate in a manner similar to the prosthetic device 10 described before to provide a free-standing artificial replacement for the root and crown portions of a tooth.

After the extraction site has been prepared in a manner generally referred to before, the implant 12a is inserted into the socket opening formed at the extraction site and positioned such that the body 124 upper face 128 is disposed generally near the outer surface formed via the gingival tissue. The gingival tissue is positioned about the adjacent portions of the implant 12a and the fastener 60 is inserted through the opening 130 in the body 124 upper surface 128, the fastener 60 being then threadedly inserted through the threaded opening 146 to a position wherein the fastener 60 head 64 is disposed near the upper face 128 of the body 124. The cap 70 is then disposed over the fastener 60 head 64 in a manner and for reasons described before with respect to the prosthetic device 10.

A temporary crown is disposed over the cap 70 and secured to adjacent teeth to maintain the implant 12a in a substantially stationary position with the socket opening during the healing period. During the healing period, blood flows about the body 124 and through the openings 136 and 138 into the space 134, the blood flowing into and through the space 134 via the openings 136 and 138. Thus, hard and soft tissue grow into and through the space 134 resulting in a bone ingrowth into the implant 12a forming a mechanical interlock between the alveolar bone and the implant 12a. As mentioned before with respect to the implant 12, some fibrous, membranous tissue may also form between portions of the newly formed and existing alveolar bone and the adjacent portions of the implant 12a further enhancing the mechanical interlock.

The hard tissue and bone ingrowth into the recess 133 provides an ingrowth engaging a circumferentially extending surface formed about the body 124 resisting movement of the implant 12a in a direction tending to remove the implant 12a from the socket opening thereby still further enhancing the mechanical interlock.

After a sufficient healing period of time to assure a mechanical interlock, the temporary crown is removed and an impression is made for the purpose of preparing the permanent crown 14a. When the crown 14a has been completed, the cap 70 and the fastener 60 are removed from the implant 12a, and the crown 14a is disposed on the body 124 upper face 128 in a position wherein the ridges 148 are disposed in the grooves 132. In this assembled position, the crown 14a is secured to the implant 12a by inserting the fastener 60 through the opening 92 into threaded engagement with the threaded opening 146, the crown 14a being secured to the implant 12a via the fastener 60 in a manner like that described before with respect to the prosthetic device 10.

It should be noted that, in one form, the lower end of the crown and the upper face of the plate or the base may be roughened to provide non-smooth surfaces such that the textured, adjacent surfaces of the crown and implant tend to resist rotational movement of the crown or, in other words, tend to secure the crown in a stationary position connected to the implant. Of course, in some applications, it may be sufficient to texture or roughen only one of the adjacent or adjoining surfaces of the crown and the implant.

Changes may be made in the various components and elements of the prosthetic device and in the steps of the prosthetic dentistry method described herein without departing from the spirit and the scope of the invention as defined in the following claims.

What is claimed is:

1. A dental prosthetic device having a portion insertable within a socket opening formed at an oral extraction site and utilizing a temporary crown or the like comprising:
   a plate having an upper face, a lower face and an opening extending through a portion thereof;
   at least two rods, one end of each rod connected to the plate and each rod extending a distance from the lower face of the plate;
   means connecting the end portions of the rods, opposite the ends of the rods connected to the plates, the rods defining an open space between the plate and the means connecting the end portions of the rods, the rods and the means connecting the end portions of the rods being insertable within the socket opening formed at the extraction site and shaped to facilitate hard and soft tissue ingrowth during a healing period within a portion of the open space and about the rods for forming a mechanical interlock;
   a crown, having an upper end and a lower end, the lower end of the crown being disposable on the upper face of the plate in one position of the dental prosthetic device and an opening extending through a portion of the crown intersecting the lower end thereof, the opening in the crown being alignable with the opening in the plate in the position of the dental prosthetic device of the crown connected to the plate;
   a base, having an upper end, a lower end, and a threaded opening intersecting the upper end and extending a distance through a portion of the base, the upper end of the base connected to the lower face of the plate and the threaded opening in the base being alignable with the opening in the plate, the connection between the base and the plate sealing the threaded opening in the base from the open space defined via the rods, whereby the temporary crown is removable securable to the plate for holding the base, the plate, the rods and the means connecting the end portions of the rods in a relatively stationary position during the healing period; and
   a fastener having a portion insertable through the opening in the crown, through the opening in the plate and threadedly engaging the threaded opening in the base, a portion of the fastener engaging a portion of the crown removably securing the crown to the plate.

2. The dental prosthetic device of claim 1 wherein the means connecting the end portions of the rods includes a portion forming an upwardly facing surface disposed within the open space between the plate lower face and the connected end portions of the rods, the hard and soft tissue ingrowth within the open space engaging the upwardly facing surface formed on a portion of the means connecting the end portions of the rods resisting the removal of the plate and the rods from the socket opening formed at the extraction site.

3. The dental prosthetic device of claim 1 wherein the base is defined further as being disposed in a portion of the open space defined via the rods and having a recess formed in a portion thereof intersecting the upper end and forming an upwardly facing surface extending circumferentially about the base between the upper and the lower ends thereof, the upwardly facing surface on the base being spaced a distance below the lower face of the plate, the hard and soft tissue ingrowth within the open space and about the recess portion of the base engaging the upwardly facing surface formed on the base for resisting removal of the plate and the rods connected thereto from the socket opening formed at the extraction site.

4. The dental prosthetic device of claim 3 wherein the base is defined further to include portions connected to a portion of each rod, generally between the ends of the rod connected to the plate and the means connecting the ends of the rods, thereby enhancing the structural integrity of the rods extending from the plate.

5. The dental prosthetic device of claim 1 wherein the rods are connected to the lower face of the plate and extend a distance therefrom toward the means connecting the end portions of the rods generally along a slightly curved path providing an overall conical shape to the plate and the rods connected thereto, the rods being spaced circumferentially about the plate and each rod being spaced from adjacent rods, the spacing between the rods providing communication with the open space defined via the rods.

6. A prosthetic dentistry method for installing a dental prosthetic device including an implant and a crown, comprising the steps of:
   preparing the socket opening at a predetermined extraction site for receiving the implant;
   inserting the implant into the socket opening;
   removable securing a threaded fastener to the implant, a portion of the fastener extending above the implant;
   inserting a cap over the portion of fastener extending above the implant;

disposing a temporary crown on the implant, a portion of the temporary crown being disposed over the cap;

securing the temporary crown in a relatively stationary position to hold the implant in a substantially stationary position during a predetermined healing period allowing hard and soft tissue ingrowth about the implant;

removing the temporary crown after the healing period;

making an impression over and about the implant to obtain the spacial disposition between the implant and adjacent teeth;

making a crown utilizing the impression to determine the required spacial disposition of the crown; and securing the crown to implant.

7. A prosthetic dentistry method for installing a dental prosthetic device including an implant and a crown, comprising the steps of:

preparing the socket opening at a predetermined extraction site for receiving the implant;

inserting the implant into the socket opening;

disposing a temporary crown on the implant and connecting the temporary crown to the implant;

securing the temporary crown to the adjacent teeth for holding the temporary crown in a relatively stationary position with respect to the adjacent teeth, thereby securing the implant in a relatively stationary position with respect to the adjacent teeth during a predetermined healing period allowing hard and soft tissue ingrowth about the implant; and securing the crown to the implant via a removable fastener extending through a portion of the crown and a portion of the implant removably securing the crown to the implant.

8. A dental prosthetic device having a portion insertable within a socket opening formed at an oral extraction site, comprising:

a plate having an upper face, a lower face and protrusions formed on the upper face thereof and extending a distance therefrom;

at least two rods, one end of each rod connected to the plate and each rod extending a distance from the lower face of the plate;

means connecting the end portions of the rods, opposite the ends of the rods connected to the plates, the rods defining an open space between the plate and the means connecting the end portions of the rods, the rods and the means connecting the end portions of the rods being insertable within the socket opening formed at the extraction site and shaped to facilitate hard and soft tissue ingrowth within a portion of the open space and about the rods for forming a mechanical interlock;

a crown, having an upper end and a lower end, disposable on the upper face of the plate in one position of the dental prosthetic device, depressions formed in the lower end of the crown and each of the protrusions on the plate being in one of the depressions in the crown and engaging adjacent portions of the crown for substantially preventing rotational movement of the crown on the plate in the one position of the crown secured to the plate; and 9. A dental prosthetic device having a portion insertable within a socket opening formed at an oral extraction site and utilizing a temporary crown or the like comprising;

a plate having an upper face, a lower face and a single opening extending through a portion thereof;

means connected to the plate and extending a distance from the lower face of the plate and defining an open space between the plate and said means connected to the plate, said means being insertable within the socket opening formed site and shaped to facilitate hard and soft tissue ingrowth during a healing period within a portion of the open space and about said means for forming a mechanical interlock;

a base, having an upper end, a lower end, and a threaded opening intersecting the upper end and extending a distance through a portion of the base, the upper end of the base connected to the lower face of the plate and the threaded opening in the base being alignable with the opening in the plate, the connection between the base and the plate sealing the threaded opening in the base from the open space defined via the rods whereby the temporary crown is removably securable to the plate for holding the base, the plate and the means connected to the plate in a relatively stationary position during the healing period; and a crown, having an upper end and a lower end, the lower end of the crown being disposable on the upper face of the plate in one position of the dental prosthetic device and an opening extending through a portion of the crown intersecting the lower end thereof, the opening in the crown being alignable with the opening in the plate in the position of the dental prosthetic device of the crown connected to the plate; and a fastener having a portion insertable through the opening in the crown and through the opening in the implant, a portion of the fastener threadedly engaging the threaded opening in the implant and a portion of the fastener engaging a portion of the crown, the fastener removably securing the crown to the plate.

10. The dental prosthetic device of claim 9 wherein the implant includes:

a body having an upper face, an opening formed through the upper face, a lower end, and an overall conical shape encompassing an open space, a plurality of spaced openings being formed through the body communicating with the open space, the hard and soft tissue forming through the openings in the body and within the open space to provide the mechanical interlock; and a rod having a threaded opening formed through and intersecting one end and extending a distance therethrough, the end intersected via the threaded opening being connected to the upper face of the body in a position aligning the threaded opening and the opening in the upper face of the body, the rod being disposed within a portion of the open space emcompassed via the body.

* * * * *